United States Patent [19]

Labovitz

[11] 4,302,402

[45] Nov. 24, 1981

[54] PROCESS FOR THE PREPARATION OF OXIMINONITRILES

[75] Inventor: Jeffrey N. Labovitz, Palo Alto, Calif.

[73] Assignee: Zoecon Corporation, Palo Alto, Calif.

[21] Appl. No.: 186,069

[22] Filed: Sep. 11, 1980

[51] Int. Cl.$^3$ ............... C07D 213/57; C07C 120/04; C07C 121/42; C07C 121/78

[52] U.S. Cl. ................... 260/465 E; 260/347.7; 260/464; 260/465.5 R; 549/75; 562/445; 562/553; 562/560; 562/577; 546/330

[58] Field of Search ............ 260/464, 465 E, 465.5 R, 260/347.7; 546/330; 549/75

[56] References Cited

U.S. PATENT DOCUMENTS 3,849,469 11/1974 Jautelat .................. 260/464
3,884,996 5/1975 Lorenz et al. .......... 260/465.5 R X

*Primary Examiner*—Dolph H. Torrence
*Attorney, Agent, or Firm*—Donald W. Erickson; Thomas T. Gordon; Jacqueline S. Larson

[57] ABSTRACT

A novel process for the manufacture of oximinonitriles which comprises the reaction of an oximinohalide with cyanide ion.

13 Claims, No Drawings

PROCESS FOR THE PREPARATION OF OXIMINONITRILES

This invention relates to a novel process for the manufacture of oximinonitriles.

Oximinonitriles are useful intermediates for the manufacture of, for example, pharmaceutical and agricultural chemiclas, such as α-ketoacids and α-aminoacids.

The process of the present invention is advantageous in that it utilizes inexpensive, readily available starting materials, thereby providing means for economically preparing oximinonitriles, which in turn allows inexpenseive preparation of α-ketocarboxylic acids and α-amino acids. An additional advantage is that the process of the present invention gives a high yield of the oximinonitrile.

The process of the present invention can be outlined as follows.

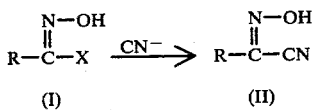

In the practice of the above outlined process, an oximinohalide of formula (I) is reacted with at least one equivalent of cyanide ion to form an oximinonitrile of formula (II). The reaction can be carried out in aqueous medium and using, for example, sodium cyanide or potassium cyanide as the source of cyanide ion. The reaction is exothermic and usually is run by starting the reaction at low temperature of the order of about −5° to 10° and then allowing the reaction temperature to warm to about room temperature. The reaction is usually complete within about 0.5 to 2.0 hours. The nitrile (II) is soluble in organic solvents and can be isolated by extraction, if desired.

The oximinonitrile (II) can be converted into an oximinocarboxylic acid of formula III by treatment with base such as NaOH or KOH in aqueous medium followed by acidification.

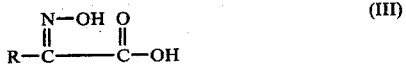

An oximinoacid of formula (III) can be hydrolyzed using sulfuric acid in the presence of formaldehyde to prepare α-ketocarboxylic acid formula (IV). The oximinoacid can also be converted directly into an α-aminocarboxylic acid of formula (V) using catalytic hydrogenation or other methods.

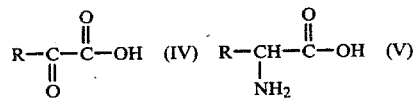

In the above outlined process, X represents bromo, chloro or iodo and R represents hydrogen or an organo group. The selection of the organo group R is not critical except as governed by the choice of selection of the α-aminoacid or α-ketoacid it is desired to manufacture. The organo group can be an aliphatic group, a heteroaliphatic group, cycloaliphatic group, an aryl group, an aralkyl group, or a heterocyclic group. The organo group can be substituted with one or more substituents such as hydroxy, mercapto, nitro, fluoro, chloro, bromo, iodo, amino and hydrocarboxy such as alkoxy. The term "aliphatic group" means branched or straight chain, alkyl of 1 to 22 carbon atoms, alkenyl of 2 to 22 carbon atoms and alkynyl of 2 to 22 carbon atoms. The term "heteroaliphatic group" means oxa-alkyl of 2 to 22 carbon atoms, and thia-alkyl of 2 to 22 carbon atoms. The term "cycloaliphatic group" means cycloalkyl of 3 to 8 carbon atoms, cycloalkalkyl of 4 to 8 carbon atoms, and cycloalkenyl of 4 to 8 carbon atoms. The term "aryl group" means aryl of 6 to 12 carbon atoms. The term "aralkyl group" means aralkyl of 7 to 12 carbon atoms. The term "heterocyclic group" means heterocyclic of 3 to 10 carbon atoms having 1 or 2 hetero atoms selected from oxygen, sulfur and nitrogen. Whenever any of the foregoing terms is modified by the term "lower", the maximum number of carbon atoms is fourteen.

The oximinohalides of formula (I) can be prepared by the reaction of an aldehyde with hydroxyamine followed by halogenation and other methods. See H. Ulrich, *The Chemistry of Imidoyl Halides,* Plenum Press, New York, p. 157 (1968) and J.H. Davies et al., *J. Chem. Soc. (C),* p. 431 (1968). Examples of oximinohalides of formula (I) include, isopropylhydroxamoyl chloride, phenylhydroxamoyl chloride, 2-propenylhydroxamoyl chloride, cyclopropylhydroxamoyl chloride, cyclopropanemethylhydroxamoyl chloride, 4-hydroxybenzylhydroxamoyl chloride, ethylhydroxamoyl chloride, hydroxymethylhydroxamoyl chloride, mercaptomethylhydroxamoyl chloride, 2-methylpropanylhydroxamoyl chloride, 2-methylbutanylhydroxamoyl chloride, acethydroxamoyl chloride (methylhydroxamoyl chloride), 4-phenylbenzhydroxamoyl chloride, trimethylacethydroxamoyl chloride, benzhydroxamoyl chloride, trifluoroacethydroxamoyl bromide, 2-methoxybenzhydroxamoyl chloride, diethylacethydroxamoyl chloride, 4-methylphenhydroxamoyl chloride, 2-pyridhydroxamoyl chloride, 2-nitrophenhydroxamoyl chloride, 2,4,6-trimethylphenhydroxamoyl chloride, 4-chlorophenhydroxamoyl chloride, 3-pyridhydroxamoyl chloride, α-furfurhydroxamoyl chloride, thiofurhydroxamoyl chloride, methylthiomethylacethydroxamoyl chloride, and 2-hydroxypropanhydroxamoyl chloride.

The present invention provides for the economical manufacture of α-oximinonitriles, α-keto acids and salts, and α-aminoacids and salts useful in, e.g., the pharmaceutical and agricultural industries such as described in U.S. Pat. Nos. 4,076,745 and 4,122,116 and Offenlegungsschrift Nos. 28 25 565, 27 08 185 and 189, 27 23 207 and 26 14 241.

The following examples are provided to illustrate the practice of the present invention. RT means room temperature. Temperature is given in degrees centigrade.

EXAMPLE 1

To a solution of 13.9 g (200 mmol) of NH$_2$OH.HCl in water at about 10°–20° is added 16.0 g (200 mmol) of 50% sodium hydroxide. To the resulting solution is added 14.4 g (200 mmol) of isobutyraldehyde. This mixture is stirred overnight at room temperature and is then cooled to 5° (in a −10° to −20° dry ice bath). To this is added chloride gas, at a rate such that the reaction mixture temperture is maintained at ~5°. After chlorine uptake has ceased, stirring is discontinued and the acidic aqueous layer is withdrawn. An aqueous solution of 10.4 g (210 mmol) of sodium cyanide is added, with stirring, to the organic layer (isopropanhydroxamoyl chloride, I; R is isopropyl, X is chloro), and the mixture is allowed to stir at RT for about two hours. It is then extracted into ether, washed with water and with brine, dried over sodium sulfate, filtered and stripped. The reaction product is purified by distillation to yield 2-oximino-3-methylbutyronitrile, b.p.=105°/15 mm. (II; R is isopropyl).

EXAMPLE 2

To 9.07 g (75 mmol) of benzaldoxime in 25 ml of carbon tetrachloride is added dropwise, at 5°, a solution of 45 ml of carbon tetrachloride saturated with 5.6 g (79 mmol) of chlorine gas. The mixture is stirred for 1 hour in an ice bath and then excess chlorine is removed by vacuum. A saturated solution of 7.35 g (150 mmol) of sodium cyanide in water is added dropwise, at 0°, to the thus-prepared phenhydroxamoyl chloride (I; R is phenyl, X is chloro). The mixture is stirred for 2 hours as it is allowed to warm to RT. An excess of aqueous sodium hydroxide is added to dissolve the product into the aqueous solution and then the carbon tetrachloride layer is discarded. The aqueous layer is acidified (HCl) and filtered, and the resulting solid is washed with water and dried to give α-oximinophenylacetonitrile, m.p.=120°-125° (II, R is phenyl).

Benzaldoxime is made by reacting benzaldehyde with NH₂OH, following the method of Example 1.

EXAMPLE 3

A solution of 3.36 g of 2-oximino-3-methylbutyronitrile, 7 ml of 50% NaOH and 3 ml of water is refluxed under a slow stream of nitrogen for several hours. This is allowed to cool to RT. The mixture is then diluted with water and washed with ether to remove the neutrals. The aqueous layer is acidified and extracted into ether to give 2-oximino-3-methylbutanoic acid, m.p. =153° (dec).

A solution of 5.24 g (40 mmol) of 2-oximino-3-methylbutanoic acid, 21 ml of 37% aqueous formaldehyde and 2 ml of conc. hydrochloric acid is stirred overnight at RT. The solution is then diluted with two volumes of water and extracted with ether (2X). The ether extracts are combined, washed with brine, dried over magnesium sulfate, filtered and stripped to yield 2-oxo-3-methylbutanoic acid, b.p. =78°/15 mm (IV; R is isopropyl).

EXAMPLE 4

To 1.60 g of 2-oximino-3-methylbutanoic acid is added 0.20 g of 10% palladium on carbon, 13 ml of methanol and 13 ml of ethanol. This mixture is stirred under 50 psi hydrogen pressure overnight at RT, followed by dilution with water, filtration and stripping to yield the amino acid valine (V; R is isopropyl).

In the same manner, 2-oximino-3-(4-hydroxyphenyl)-propanoic acid is reacted with 10% palladium on carbon, methanol and ethanol to give the amino acid tyrosine.

EXAMPLE 5

Following the procedure of Example 1 or 4, each of 4-hydroxybenzhydroxamoyl chloride, cyclopropanhydroxamoyl chloride, acethydroxamoyl chloride, and methylthiomethylacethydroxamoyl chloride is reacted with NaCN to form 2-oximino-3-(4-hydroxyphenyl)-propylnitrile, α-oximino-cyclopropylacetonitrile, α-oximino-methylacetonitrile and 2-oximino-4-methylthiobutyronitrile.

What is claimed is:

1. A process for the manufacture of oximinotriles which comprises the reaction of an oximinohalide with cyanide ion in an aqueous medium.

2. The process according to claim 1 wherein the oximinonitrile is of the following formula (II)

and the oximinohalide is of the following formula (I)

wherein X is bromo, chloro or iodo and R is hydrogen or an organo group.

3. The process according to claim 2 wherein the reaction is conducted at a temperature of from about 0° to room temperature.

4. The process according to claim 3 wherein the cyanide ion is derived from sodium cyanide or potassium cyanide in aqueous medium.

5. The process according to claim 4 wherein R is an aliphatic group, heteroaliphatic group, a cycloaliphatic group, an aryl group, an aralkyl group, or a heterocyclic group.

6. The process according to claim 5 wherein R is an alkyl group or heteroalkyl group.

7. The process according to claim 5 wherein R is an aryl group or an aralkyl group.

8. The process according to claim 6 wherein X is chloro.

9. The process according to claim 7 wherein X is chloro.

10. The process according to claim 4 wherein R is isopropyl.

11. The process according to claim 4 wherein R is isopropyl and X is chloro.

12. The process according to claim 8 wherein R is a lower alkyl group.

13. The process according to claim 9 wherein R is a phenyl group.

* * * * *